United States Patent
Lima De Miranda

(10) Patent No.: US 10,061,198 B2
(45) Date of Patent: Aug. 28, 2018

(54) METHOD FOR PRODUCING A MEDICAL DEVICE OR A DEVICE WITH STRUCTURE ELEMENTS, METHOD FOR MODIFYING THE SURFACE OF A MEDICAL DEVICE OR OF A DEVICE WITH STRUCTURE ELEMENTS, MEDICAL DEVICE AND LAMINATED COMPOSITE WITH A SUBSTRATE

(71) Applicant: ACQUANDAS GMBH, Kiel (DE)

(72) Inventor: Rodrigo Lima De Miranda, Kiel (DE)

(73) Assignee: Acquandas GmbH, Kiel (DE)

( * ) Notice: Subject to any disclaimer, the term of this patent is extended or adjusted under 35 U.S.C. 154(b) by 324 days.

(21) Appl. No.: 14/907,399

(22) PCT Filed: Jul. 25, 2014

(86) PCT No.: PCT/EP2014/066006
§ 371 (c)(1),
(2) Date: Jan. 25, 2016

(87) PCT Pub. No.: WO2015/011253
PCT Pub. Date: Jan. 29, 2015

(65) Prior Publication Data
US 2016/0170306 A1    Jun. 16, 2016

(30) Foreign Application Priority Data

Jul. 25, 2013  (DE) .................. 10 2013 107 947

(51) Int. Cl.
*A61B 17/32* (2006.01)
*G03F 7/40* (2006.01)
(Continued)

(52) U.S. Cl.
CPC ............... *G03F 7/40* (2013.01); *A61B 17/32* (2013.01); *A61L 31/022* (2013.01);
(Continued)

(58) Field of Classification Search
CPC ........................................... H01L 21/00
See application file for complete search history.

(56) References Cited

U.S. PATENT DOCUMENTS

| | | | |
|---|---|---|---|
| 2002/0091438 | A1 | 7/2002 | Trozera |
| 2002/0096727 | A1 | 7/2002 | Fischer |

(Continued)

FOREIGN PATENT DOCUMENTS

| | | |
|---|---|---|
| DE | 10065013 A1 | 7/2002 |
| DE | 10151130 C1 | 2/2003 |

(Continued)

OTHER PUBLICATIONS

Written Opinion of the International Search Authority, International Search Report, Translation of the ISR for application WO2015011253.

(Continued)

*Primary Examiner* — Timon Wanga
(74) *Attorney, Agent, or Firm* — Hassan Abbas Shakir; Katten Muchin Rosenman LLP

(57) ABSTRACT

A medical device with structure elements is made by providing a substrate; optionally depositing a layer of a sacrificial material on the substrate; and applying of a photoresist layer to the substrate. The layer of sacrificial material and structuring of the photoresist layer according to the shape of the structure elements are produced such that first free spaces are formed which are open on the side facing away from the substrate and are delimited by side faces of the photoresist layer. An angle is set between the side faces and the substrate. Sacrificial material is deposited in the first free spaces so first mask elements from sacrificial material are adapted to the inner contour of the first free spaces. The photoresist layer is removed so that second free spaces are formed between the first mask elements.

18 Claims, 11 Drawing Sheets

(51) Int. Cl.
    *G03F 7/00*     (2006.01)
    *G03F 7/20*     (2006.01)
    *A61L 31/02*     (2006.01)
    *A61L 31/08*     (2006.01)
    *H01L 21/00*     (2006.01)
    *A61F 2/82*     (2013.01)
    *A61B 17/00*     (2006.01)

(52) U.S. Cl.
    CPC .............. *A61L 31/088* (2013.01); *G03F 7/00* (2013.01); *G03F 7/0035* (2013.01); *G03F 7/0037* (2013.01); *G03F 7/201* (2013.01); *A61B 2017/00526* (2013.01); *A61F 2/82* (2013.01); *A61L 2400/16* (2013.01); *A61L 2420/02* (2013.01); *H01L 21/00* (2013.01)

(56) References Cited

U.S. PATENT DOCUMENTS

| | | | |
|---|---|---|---|
| 2005/0233503 A1 | 10/2005 | Leib | |
| 2007/0275502 A1* | 11/2007 | George | B81C 1/00333 |
| | | | 438/106 |
| 2010/0009142 A1* | 1/2010 | Quandt | A61L 27/06 |
| | | | 428/209 |
| 2010/0044212 A1* | 2/2010 | Kim | B81B 3/0021 |
| | | | 204/192.12 |
| 2011/0308957 A1 | 12/2011 | Specht | |
| 2012/0040528 A1* | 2/2012 | Kim | H01L 21/76816 |
| | | | 438/675 |
| 2012/0319205 A1* | 12/2012 | Hempel | H01L 21/823842 |
| | | | 257/368 |
| 2013/0003319 A1* | 1/2013 | Malatkar | H01L 25/16 |
| | | | 361/746 |
| 2013/0157441 A1* | 6/2013 | Han | H01L 21/02532 |
| | | | 438/478 |
| 2013/0171821 A1* | 7/2013 | Kim | H01L 21/76877 |
| | | | 438/675 |

FOREIGN PATENT DOCUMENTS

| | | |
|---|---|---|
| DE | 10222609 | 11/2003 |
| DE | 102010024498 A1 | 12/2011 |
| EP | 2395395 A2 | 12/2011 |
| WO | 9845506 A1 | 10/1998 |
| WO | 200073241 A1 | 12/2000 |
| WO | 2005098486 A1 | 10/2005 |
| WO | 2007089204 A1 | 8/2007 |
| WO | 2008000467 A1 | 1/2008 |
| WO | 2009150610 A1 | 12/2009 |

OTHER PUBLICATIONS

Office Action issued in the corresponding German patent application No. 10 2013 107 947.4 dated Feb. 13, 2014, machine translation of a portion of the office action is provided.

English Translation of the International Preliminary Report on Patentability of PCT/EP2014/066006 dated Feb. 4, 2016.

* cited by examiner

⊢100 μm⊣

⊢30 μm⊣

METHOD FOR PRODUCING A MEDICAL DEVICE OR A DEVICE WITH STRUCTURE ELEMENTS, METHOD FOR MODIFYING THE SURFACE OF A MEDICAL DEVICE OR OF A DEVICE WITH STRUCTURE ELEMENTS, MEDICAL DEVICE AND LAMINATED COMPOSITE WITH A SUBSTRATE

BACKGROUND

1. Field of the Invention

The invention relates to a method for producing a medical device having structural elements or a device having structural elements, to a method for modifying the surface of a medical device or of a device having structural elements, to a medical device having a sharp-edged structure and a laminated composite having a substrate.

2. Discussion of the Related Art

Medical devices, for example stents, typically have complex structures on account of which the medical device achieves particularly high flexibility. Flexibility enables conveying in the catheter and positioning of the device within a hollow organ of the body. Flexibility furthermore facilitates the behavior of the medical device in tightly curved vessels. Various methods are used for manufacturing medical devices of this type, in particular for the structure. Apart from braiding wire elements, the devices are also cut from a solid material by laser methods. Furthermore, US 2002/0091438 A1 discloses utilization of an etching method for forming the structures. Here, structures are generated by forming voids in a thin material plate. The voids here are formed by the etching method.

In the method described in US 2002/0091438 A1, a tube is initially covered by a uniformly thick photoresist layer. The photoresist is subsequently cured by UV light in those regions in which the webs of the medical device to be produced, for example of the stent, are disposed. The cured photoresist thus depicts the later structure of the stent. In the following step, the coated tube is submerged for a specific period of time in a bath containing a solvent. The non-cured points of the photoresist layer are released in the solvent, so that the material of the tube becomes visible again in those regions. The exposed points of the tube are removed in a subsequent electrochemical etching process. Thus, only the webs of the stent, which are covered with the cured photoresist, remain.

SUMMARY OF THE INVENTION

The present invention is based on the object of stating an improved method for producing a medical device or a device with structural elements, in which method the contour of the structural elements and the material properties may be better influenced. Moreover, the invention is based on the object of stating a method for modifying the surface of a medical device having structural elements, or a device having structural elements. Furthermore, a medical device which is suitable for cutting tissue or debris in vessels is to be stated by way of the present invention. Furthermore, a laminated composite having a substrate and a sacrificial material layer for producing a medical device or a device having structural elements is to be stated by way of the invention.

The invention is based on the concept of stating a method for producing a medical device having structural elements, the method comprising the following method steps:

providing a substrate;
optionally deposition-placing a layer of a sacrificial material on the substrate;
applying a photoresist layer to the substrate, in particular to the sacrificial material layer;
structuring the photoresist layer according to the shape of the structural elements to be produced, so that first voids which are open on that side that faces away from the substrate and which are delimited by lateral faces of the photoresist layer are formed, wherein an angle between the lateral faces and the substrate is set;
deposition-placing sacrificial material, so that first masking elements of sacrificial material, which are adapted to the internal contour of the first voids, are formed in the first voids;
removing the photoresist layer, so that second voids are formed between the first masking elements;
deposition-placing, in particular by vapor deposition, a first material of the device to be produced in the second voids and on the upper side of the first masking elements; and
removing the sacrificial material and/or performing further process steps.

The invention moreover is based on the concept of stating a method for producing a device having structural elements, in particular for producing actuators and/or micro pumps, linear actuators in the field of microsystems technology (MEMS) and/or actuators for minimally invasive instruments and/or micro actuators and/or flexible micro antennae, the method comprising the method steps already mentioned.

The micro pumps to be produced may be used or employed, respectively, in fluidics, for example. The actuators to be produced for minimally invasive instruments may be used or employed, respectively in the context of guidable hypo tubes and/or catheters, for example.

The following description is directed toward individual method steps of the methods according to the invention, that is to say that the former refers to both the method for producing a medical device as well as to the method for producing a device having structural elements. In this way, the individually described method steps may also be performed in the production of a device having structural elements, despite explicit reference potentially being made to a medical device.

The method or the methods, respectively, has/have the advantage that the material properties may be set in a targeted manner during deposition-placing, in particular in physical vapor deposition. In this way, it is possible for the microstructure properties to be set in a wider range than is possible in a molten-metallurgical manner, for example. Contamination of the material may be better avoided, since deposition-placing usually takes place under a vacuum. Moreover, additional heat-treatment steps which are required in the prior art in order for the microstructure changes which are created during rolling of the solid material, or generally during the mechanical treatment of the solid material, to be influenced, may be dispensed with.

Moreover, the invention by way of the configuration of the masking elements enables various types of profiling on the structural elements, so that both the geometry as well as the material properties of the structural elements according to the invention may be set. The combination of a PVD method and the masking elements which are structured according to the invention enables the production of self-supporting profiled structural elements or webs, respectively, of a stent, which in addition to the geometry have excellent material properties.

In principle, the substrate may be formed from any arbitrary material. The substrate should have as smooth a surface as possible, since the properties of the surface of the substrate influence the surface of the medical device to be produced. A surface which is as smooth as possible is desirable, so that the substrate preferably has materials in which these properties are inherent. The substrate may preferably be composed of glass, silicon, and/or quartz. The method according to the invention for producing the medical device comprises optionally deposition-placing a first layer of a sacrificial material on the substrate. This feature is optional because the provided substrate may have already been produced from the sacrificial material. In this case, deposition-placing the first sacrificial material layer is not mandatory.

Preferably, the sacrificial material layer is electrically conducting. It may be formed from copper, for example. The thickness of the layer is >1 nm.

In the following step, a photoresist layer is applied to the substrate or to the optional sacrificial material layer, respectively. The resist used may be a photoresist which may be structured in the context of a lithographic method. Preferably, a radiation-sensitive lacquer, which is cured by exposure with UV light, for example, is used. The photoresist layer is subsequently structured, so that the photoresist layer or the structure of the structured photoresist layer, respectively, replicates the shape of the structural elements to be produced of the medical device. Structuring or the structure, respectively, of the photoresist is created by dissimilar illumination and thus curing of the photoresist.

The structure is generated in that the photoresist is cured at those points and regions at which the material of the medical device to be produced will be deposition-placed later in the method. Curing may be carried out by various illumination methods. Established illumination methods are, for example, electron-beam lithography and x-ray lithography. Optical lithography (photolithography) is preferable. A photomask which covers the various regions of the photoresist and thus forms shadows is used during exposure. The formation of shadows leads to the UV light not contacting the photoresist and thus also not leading to curing of the photoresist. The shape of the photomask thus contributes toward influencing the predetermined structure of the medical device. The structure of the photomask thus corresponds to the structure of the medical device to be produced. Furthermore, parameters of the illumination method, for example the exposure time, the intensity of illumination, or the distance of the illumination source from the medical device may be set. Ultraviolet light (UV light) is preferably used as an illumination means. The incident angle of the UV light may likewise be set, so that curing of the photoresist which depends on the incident angle of the UV light is performed. On account thereof, the angle between the lateral faces of the photoresist layer and the substrate or the first sacrificial material, respectively, is adjustable.

After curing of the photoresist, the non-cured regions of the photoresist are removed. A cured photoresist layer which at least partially corresponds to the structural elements of the medical device remains on the substrate. The lateral faces of the photoresist layer likewise at least partially correspond to the lateral faces of the structural elements of the medical device. The removed regions of the photoresist layer form first voids.

A further sacrificial material is deposition-placed in the following step. The further sacrificial material may be composed of the same material of which the first sacrificial material layer is also composed. Preferably, the second sacrificial material comprises an electrically conducting material, in particular copper. Deposition-placing of the sacrificial material is performed substantially in the first voids. Here, first masking elements are created from the sacrificial material. These masking elements are adapted to the internal contour of the first voids. The shape of the masking elements influences the profile shape of the structural elements of the device to be produced. In principle, deposition-placing of the sacrificial material may be performed by way of any arbitrary deposition method. However, an electrochemical deposition method, in particular a galvanic deposition method is preferably used. The galvanic deposition method enables growth of the masking elements in such a manner that the masking elements are adapted to the internal contour of the first voids.

In a following step, the photoresist layer is removed. On account thereof, second voids are created between the first masking elements.

In the next method step, a first material of the device to be produced is deposition-placed. Deposition is preferably performed by a physical vapor deposition-placing method such as sputtering. Sputtering is particularly well suited in order for the material properties of the device, in particular of the structural elements, to be set in a targeted manner.

The first material of the device to be produced here is deposition-placed in the second voids and on the upper side of the first masking elements. In other words, the second voids are filled with the first material of the device to be produced. Deposition-placing the first material on the upper side of the first masking element generates an almost rectangular profile of the deposition-placed layer. However, in the second voids the first material is deposition-placed in such a manner that profiled elements are formed. The profiling of the structural elements is influenced by the inclination of the walls of the first masking elements.

The sacrificial material is removed in the next method step. Further process steps may be carried out alternatively or else additionally thereto. Removal of the sacrificial material may be performed by way of various etching methods. Wet-chemistry based etching and dry etching methods are known, for example. While the sacrificial materials are indeed removed by way of the etching methods, the first material of the device to be produced is however not corroded. Therefore, only the first material of the device to be produced remains after removal of the sacrificial material.

In one preferred embodiment of the invention it is provided that the angle between a lateral face and the substrate is 45 degrees to less than 90 degrees.

In principle, the angle between a lateral face and the substrate may be an arbitrary angle. Furthermore, angles between a lateral face and the substrate are also possible between 30 degrees and 135 degrees. Furthermore, the two lateral faces of a void in relation to the substrate may have dissimilar angles. This design embodiment leads to the medical device to be produced having structural elements which in the cross section are asymmetrical. A first lateral face of the structural element may be more heavily inclined than the second lateral face of the structural element.

According to one further design embodiment of the invention, it is provided that the lateral faces of in each case one void are opened in a funnel-shaped manner. The void which is created by the structuring of the photoresist tapers off toward the substrate, and the spacing of the lateral faces decreases. The further void which is delimited by the masking elements is at least in portions the negative image of the void in the photoresist and widens toward the substrate.

According to one preferred design embodiment of the invention it is provided that the first masking elements have flanks which are inclined so as to correspond to the angle of the lateral faces.

The masking elements in the first voids are formed by the deposition of the sacrificial material. In other words, the lateral faces of the photoresist layer act like a shape-imparting installation which guides the sacrificial layer into a specific shape as deposition-placing takes place. The lateral faces of the photoresist thus mold the flanks of the first masking element.

According to one design embodiment of the present invention, it is provided that the photoresist layer is structured in such a manner that the profile of web-like structural elements, in particular the profile of the webs in a lattice structure, is replicated. On account of the structuring of the photoresist layer, trenches are formed in the photoresist layer. The second sacrificial material may be deposition-placed into these trenches. On account of the structuring of the photoresist, the profile of the web-like structural elements is thus determined and formed in a particularly simple manner.

According to one design embodiment of the present invention, the following method steps are furthermore provided:
  optionally deposition-placing a further sacrificial material layer on the material of the device to be produced;
  applying a further photoresist layer;
  structuring the further photoresist layer according to the shape of a surface profiling of the structural elements to be produced;
  deposition-placing sacrificial material, so that at least one further second masking element which is adapted to the external contour of the structured further photoresist layer is formed;
  removing the photoresist layer and the optional further sacrificial material layer, so that a third void which exposes the material of the device to be produced and which is delimited by the further masking element or by a plurality of further masking elements is formed;
  deposition-placing, in particular by vapor deposition, the first or a second material of the device to be produced in the third void; and
  removing the sacrificial material.

On account of extending the method as has previously been described by way of the abovementioned method steps, profiling of the surface of the medical device and/or of the device having structural elements is enabled.

This surface profiling is particularly advantageous in the context of the previously described method, since the former may be carried out immediately after production of the structural elements in one working step.

Initially and optionally, a further sacrificial material layer is deposition-placed on the material of the device to be produced. Subsequently, a further photoresist layer is applied and structured. Here, structuring of the further photoresist layer corresponds to the surface profile of the structural elements to be produced. This structuring of the photoresist layer is substantially performed like the structuring of the first photoresist layer, as has already been described above.

Subsequently, a further sacrificial material is deposition-placed, so that a masking element is formed. By way of the external contours of the structured photoresist layer, a shape which is formed so as to be complementary to the structured photoresist layer is molded onto the masking element.

In the next step, the photoresist layer and the optional further sacrificial material layer are removed, so that a third void is formed. The third void extents up to the material of the device to be produced. In this way, the third void in the direction of the substrate is delimited by the first material of the device to be produced. In the horizontal direction, that is to say in a direction parallel to the substrate, the third void is delimited by the further masking element or by the plurality of further masking elements, respectively.

In a next step, the first or else a second material of the device to be produced is deposition-placed in the third void. Deposition-placing here is preferably performed by a physical vapor deposition method, in particular by sputtering.

The remaining sacrificial material is subsequently removed or disposed of, respectively.

It is also possible for the surface profiling to be applied in the context of another production method, for example of a conventional etching method or a laser cutting method. In this case, the finished device which has been produced elsewhere is subjected to the surface profiling, wherein only the terminology has been adapted. For example, a structure may be sputtered onto a stent in this way.

According to one preferred design embodiment of the invention, it is provided that during structuring of the further photoresist layer an angle is set between the lateral faces of the further photoresist layer and of the further sacrificial material layer. On account of this design embodiment, the lateral faces of the surface profiling of the structural elements to be produced may be influenced. Here, the angle of the further photoresist layer approximately corresponds to the angle of the surface profiling to be produced.

In one preferred design embodiment of the invention, it is provided that the sacrificial material layer, in particular the sacrificial material layers, is/are electrically conducting and the masking elements are electrochemically deposition-placed on the electrically conducting sacrificial material layers. The design of the masking elements is simplified on account of the use of an electrochemical deposition method.

According to one preferred design embodiment of the invention, it is provided that the material of the device to be produced is deposition-placed by sputtering.

According to one preferred design embodiment of the invention, it is provided that the height of the masking elements, in particular of the first and second masking elements, is set for influencing the maximum height of the structural elements to be produced. Here, the maximum height of the structural elements may be greater than the height of the masking elements, for example by 1 to 20%. It is also possible for the void between the masking elements to not be completely filled, so that the height of the structural elements is less than the height of the masking elements, for example by 10 to 20%. Furthermore, the structural elements may terminate so as to be flush with the masking elements. The height of the masking elements thus determines the range within which the maximum height of the structural elements may lie.

Furthermore, the height of the masking elements influences the shape of the structural elements. Since the individual masking elements widen in a direction leading away from the substrate, the spacing of the upper side of the masking elements decreases as the height increases. The higher the masking elements, the more pointed the cross section of the structural elements. As the height increases, the void between the masking elements and thus the cross-sectional profile of the structural elements thus approximates a triangular shape.

According to one particularly preferred design embodiment of the invention, it is provided that the spacing of the first masking elements is set for influencing the width of the structural elements to be produced. By way of the mutual spacing of the masking elements, the width of the structural elements to be produced may be set in a targeted manner. The larger the mutual spacing of the masking elements, the wider the structural elements to be produced of the medical device. The shape of the cross section of the structural elements is also influenced by way of the mutual spacing of the masking elements. On account thereof, the shape of the cross section is thus also adjustable. The upper side of the structural element by way of the mutual spacing of the masking elements may be designed so as to be wider or narrower. As the mutual spacing of the masking elements increases, the upper side of the structural element becomes wider. The shape of the cross section of the structural element thus tends to be trapezoidal. As the mutual spacing of the masking elements decreases, the upper side of the structural element becomes narrower. The shape of the cross section of the structural element thus tends to be triangular. The cross section of the structural element to be produced may thus be set in a targeted manner by way of the design of the masking elements. Here, the following factors in particular play a part: the height of the masking elements, the mutual spacing of the masking elements, and the angle of the flanks of the masking elements which determines the funnel shape of the masking elements. The cross-sectional shape of the structural elements is adjusted by way of the targeted setting of these factors.

According to one preferred design embodiment of the invention, it is provided that the first and/or second masking elements have a height of 2 to 100 μm. On account thereof, the structural elements of the device to be produced may be formed so as to have a height of 2 to 100 μm.

According to one preferred design embodiment of the invention, it is provided that the first material of the medical device or of the device having a structural element and/or the second material of the medical device or of the device having a structural element comprise(s) a shape-memory material, in particular nitinol (NiTi), and/or a heavy metal, in particular tantalum, and/or an electrically conducting material.

According to one preferred design embodiment of the invention, it is provided that the first material of the medical device has a shape-memory material, and that the second material of the medical device has a heavy metal. On account thereof, a medical device in the form of a stent may be formed, for example, said medical device by means of the heavy metal, for example, tantalum, comprising an x-ray resistant material, such that the stent may also be easily detected when within the body.

The second material of the medical device may also be completely deposition-placed on the first material of the medical device. The second material of the medical device has no profiling but rather forms a second layer which bears on the first material of the medical device and completely covers the latter. Subsequently, a third material of the medical device may be deposition-placed, so that the third material in turn at least partially covers the second material of the medical device. For example, the second material of the medical device may be an electrically conducting material which at points is covered by the third material, so that contact points which are exposed are formed in the bare regions which are not covered by the third material. The exposed points may thus be in contact with a vessel wall, for example.

According to one coordinate design embodiment of the invention, a medical device which is produced by one of the previously described methods is provided. Here, the structural elements of the medical device have at least one inclined lateral wall having a cutting edge which is formed between the lateral wall and a base area of the structural element, wherein the cutting edge projects beyond the face of the lateral wall and has a curved flank which continuously transitions into the face of the lateral wall. The base area is that face (external face) that in the implanted state faces the vessel wall. The cutting edge is formed in that the curved flank converges with the base area and at the free end forms a tip. The tip in the longitudinal direction extends along the lateral wall. The center point of the curvature of the flank lies outside the structural element (concave curvature).

The cutting edge may be used to remove debris in a vessel. Furthermore, the cutting edge may form a barb which cuts into the tissue so as to anchor the device in a vessel wall and to prevent dislocation thereof.

According to a coordinate design embodiment of the invention, a laminated composite having a substrate and a sacrificial material layer, for producing a medical device having structural elements is provided, wherein the sacrificial material layer is disposed on the substrate, and masking elements of a sacrificial material are formed on the sacrificial material layer, the flanks of said masking elements having an angle which is formed so as to be complementary to the angle of the lateral walls of the device to be produced, wherein the spacing between the masking elements corresponds to the width of a structural element of the device to be produced.

According to a further coordinate aspect of the invention, a laminated composite having a substrate and a sacrificial material layer, for producing a device having structural elements, in particular for producing actuators and/or micro pumps and/or linear actuators in the field of microsystems technology and/or actuators for minimally invasive instruments and/or micro actuators and/or flexible micro antennae is provided, wherein the sacrificial material layer is disposed on the substrate, and masking elements of a sacrificial material are formed on the sacrificial material layer, the flanks of said masking elements having an angle which is formed so as to be complementary to the angle of the lateral walls of the device to be produced, wherein the spacing between the masking elements corresponds to the width of a structural element of the device to be produced.

As has already been set forth in the context of the method, the sacrificial material layer may also be optionally provided. In this case, the substrate typically has the respective desired properties, so that a sacrificial material layer is superfluous. In this case, the masking elements are formed directly on the substrate.

The laminated composite described enables the production of a medical device having profiled structural elements in a simple manner. The structural elements on the lateral faces have angles which correspond to the angles of the flanks of the masking elements.

BRIEF DESCRIPTION OF THE INVENTION

The invention will be set forth in more detail in the following by means of exemplary embodiments with reference to the appended drawings. In the drawings.

DETAILED DESCRIPTION OF THE INVENTION

Figure 1:
FIG. 1 shows a substrate having a first sacrificial material deposition-placed thereon.

FIG. 1 shows the substrate 3 having a deposition-placed sacrificial material 4, for example copper. The substrate has a smooth surface, that is to say a surface having very little surface roughness.

Figure 2:
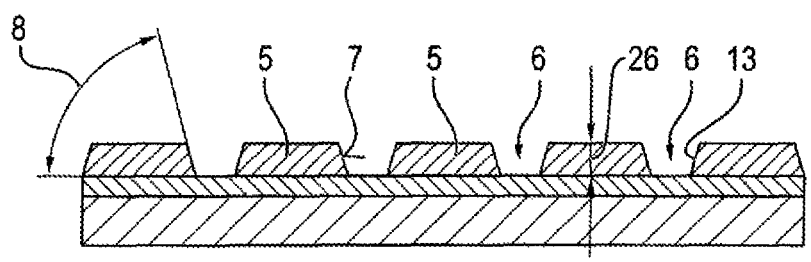
FIG. 2 shows a section through the substrate of FIG. 1, having the deposition-placed sacrificial material and having a structured photoresist layer.

FIG. 2 shows the laminated composite of FIG. 1, wherein the former has a structured photoresist layer 5. The photoresist layer 5 is applied to the sacrificial material layer 4 and structured. The structured photoresist layer 5 has first voids 6 which are delimited by lateral faces 7. In relation to the substrate 3, the lateral faces 7 form an angle 8. On account thereof, an internal contour 13 of the voids 6 results. The voids 6 on that side that faces away from the substrate 3 are open. The voids thus form open trenches. Structuring of the photoresist layer 5 is performed by an illumination method, in particular by UV lithography. To this end, the photoresist layer 5 is exposed with a UV light, for example. The delimitations between the exposed and non-exposed regions of the photoresist 5 are generated by a photomask (not illustrated). The photomask in regions shades the photoresist, so that the UV light does no longer penetrate through to the photoresist. In the present exemplary embodiment, the lateral faces 7 of the first voids 6 which are configured in the photoresist 5 form an angle 8 of approximately 60 degrees. This angle 8 is generated in that the UV light is incidental on the photoresist at a corresponding angle.

Figure 3:
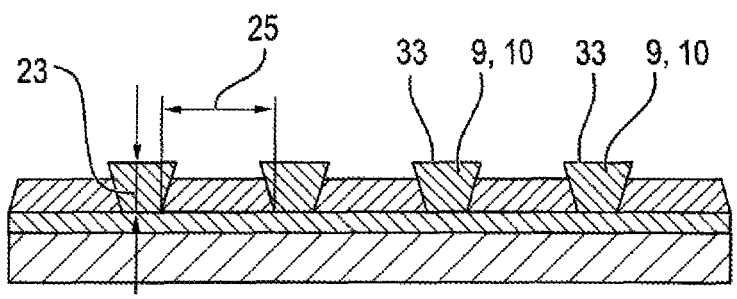
FIG. 3 shows the laminated composite of FIG. 2, having a deposition-placed second sacrificial material.

A further method step in which a further sacrificial material is deposition-placed by way of a galvanic deposition method on the illustrated laminated composite is illustrated in FIG. 3. It can be seen from FIG. 3 that masking elements 10 having an upper side 33 are formed by the galvanic deposition method. The upper side 33 forms a free face which faces away from the substrate. The masking elements 10 fill the voids 6 and in the present exemplary embodiment rise beyond the height 26 of the photoresist layer 5. During deposition-placing of the sacrificial material 9, the lateral faces 7 of the photoresist layer 5 generate the inclined flanks 14 of the first masking elements 10. The masking elements 10 extend away from the substrate in a direction which is perpendicular to the latter. The respective masking element 10 at that end thereof that faces the substrate 3 is as wide as the void 6 on the base area thereof or on that face thereof that is adjacent to the sacrificial material 4. The first masking element 10 in the profile of the height becomes wider and forms a wedge-shaped cross section.

Figure 4:
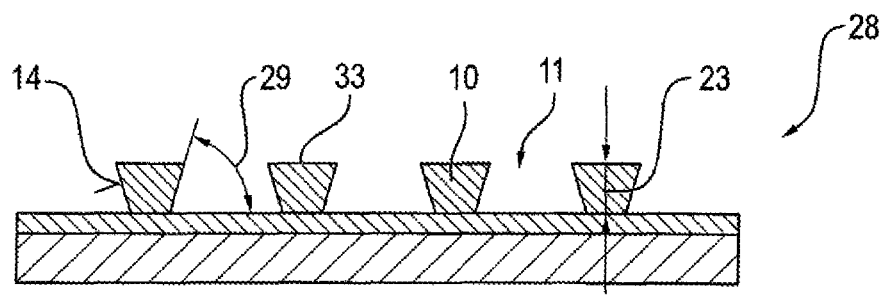
FIG. 4 shows the laminated composite of FIG. 3, having the photoresist layer removed.

FIG. 4 shows the laminated composite according to FIG. 3 at a method stage at which the photoresist has been removed. The photoresist is preferably removed with acetone or with a similar solvent. The substrate 3, the sacrificial material 4 bearing on the substrate 3, and the masking elements 10 which are formed from the sacrificial material 9 remain. In relation to the substrate, the flanks of the masking elements 10 form an angle 29. The masking angle 29 is complementary to the photoresist angle 8. Second voids 11 have now been formed between the masking elements 10.

Figure 5:
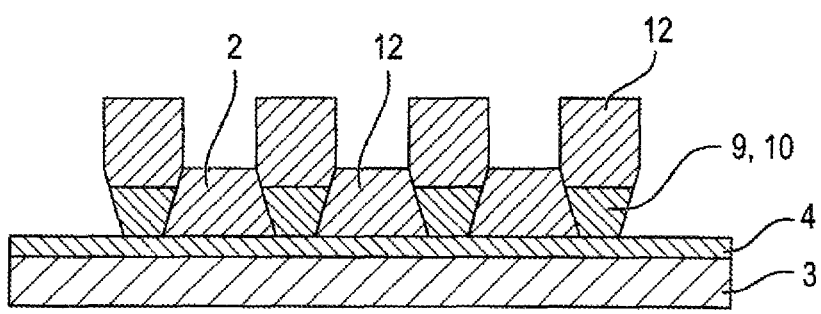
FIG. 5 shows the laminated composite of the device to be produced, having a first deposition-placed material.

FIG. 5 shows the laminated composite 28 of FIG. 4, wherein in a further method step a first material 12 of the device to be produced has been deposition-placed in the second voids 11 between the masking elements 10, and on the upper side 33 of the masking elements 10. In this state the medical device is already apparent, wherein the structural elements 2 of the medical device are replicated here.

Figure 6:
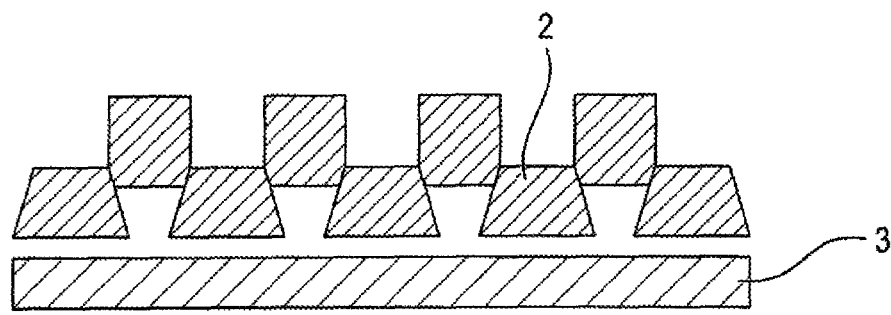
FIG. 6 shows the structural elements of the medical device to be produced, after removal of the sacrificial material.

FIG. 6 now shows the medical device or the structural elements 2, respectively, after the entire sacrificial material 4, 9 has been removed. To this end, nitric acid ($HNO_3$) is used in the etching method, for example. The structural elements of the medical device remain.

Figure 7:
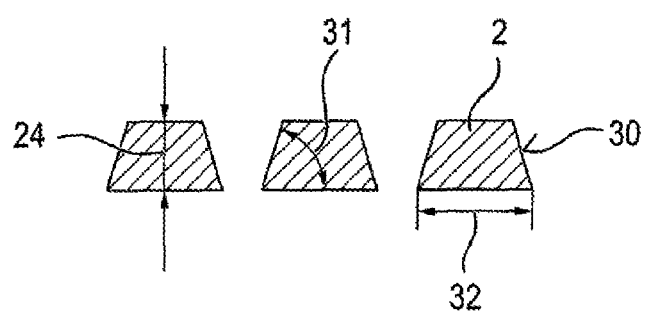
FIG. 7 shows the self-supporting medical device in the final stage thereof.

FIG. 7 shows the finished structural elements 2 of the medical device. The structural elements 2 may be the webs of a lattice structure, for example. The lattice structure may be of a closed tubular type and may form a stent or a thrombectomy device, for example. The other structural elements of the lattice structure, which have been produced in a corresponding manner, are not illustrated in FIG. 7. The dimensions such as the height 24, the angle 31 of the lateral walls, and the width 32 of the base area of the structural elements 2 are shown.

The structural elements 2 are produced so as to be self-supporting by way of a PVD method. Self-supporting means that no other basic material which has been produced in a dissimilar manner is used as a supporting structure for a PVD coating but rather that the entire structural element 2 has been produced by the PVD method.

Figure 8:
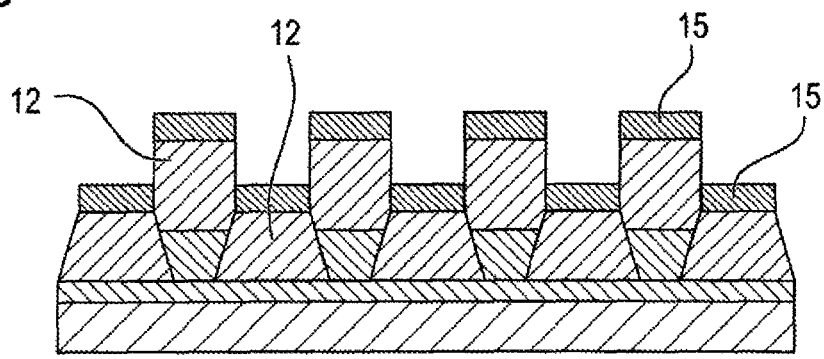
FIG. 8 shows the laminated composite of FIG. 5, wherein a further sacrificial material layer has been deposition-placed.

The method by way of which surface profiling of the medical device is possible is shown in selected method steps in FIGS. 8 to 15. FIG. 6 shows the medical device or the structural elements 2, respectively, as still disposed on the laminated composite of FIG. 4 or FIG. 5, respectively. As is shown in FIG. 8, a further sacrificial material 15 is deposition-placed on the structural elements 2. The sacrificial material 15 covers the entire first material 12 of the device to be produced.

Figure 9:
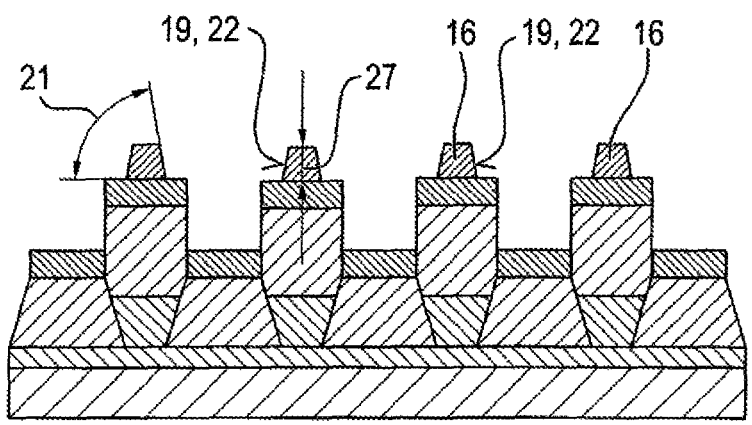
FIG. 9 shows the laminated composite of FIG. 8, wherein a structured photoresist has been applied.

FIG. 9 shows the next method step for producing a surface profiling of the structural elements 2 to be produced. An already structured further photoresist layer 16 is shown. The lateral faces 22 of the further photoresist layer 16 in relation to the further sacrificial material layer 15 form an angle 21. The structuring of the photoresist layer 16 substantially forms a positive image of the desired surface profiling 34 of the structural element to be produced. The structured photoresist layer 16 may form insular elevations, for example, which are disposed so as to be distributed along the surface of the structural elements. This shape corresponds to the profile of the modified surface of the structural elements 2. Suitable structuring of the photoresist layer enables any other surface profiles.

Figure 10:
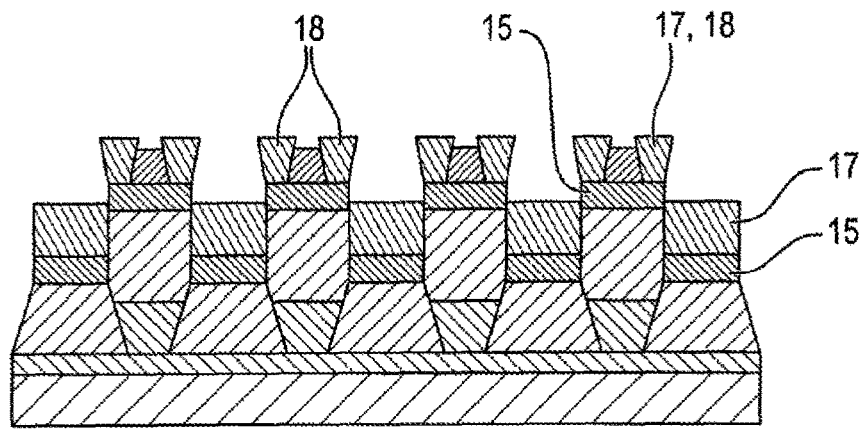
FIG. 10 shows the laminated composite of FIG. 9, wherein a further sacrificial material layer has been applied.

FIG. 10 shows the subsequent method step in which a further sacrificial material layer 17 has been applied. The sacrificial material layer 17 forms further masking elements 18 which are formed around the photoresist layer 16. The internal contour of the masking elements 18 corresponds to the external contour of the structured photoresist layer.

Figure 11:
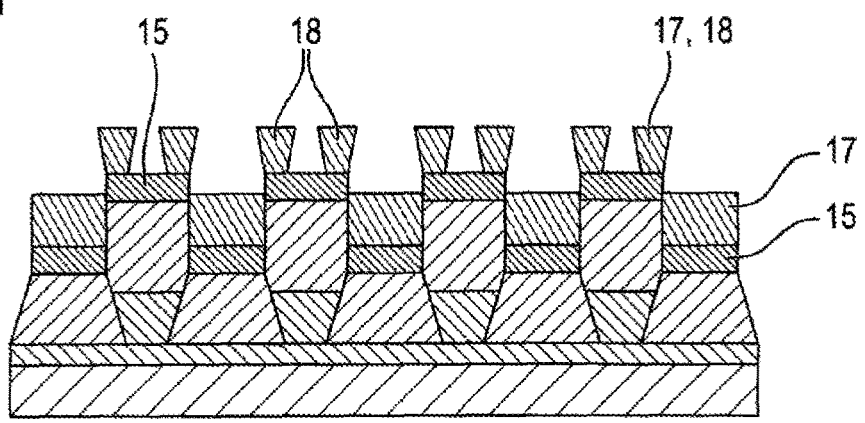
FIG. 11 shows the laminated composite of FIG. 10, wherein the photoresist layer has been removed.
Figure 12:
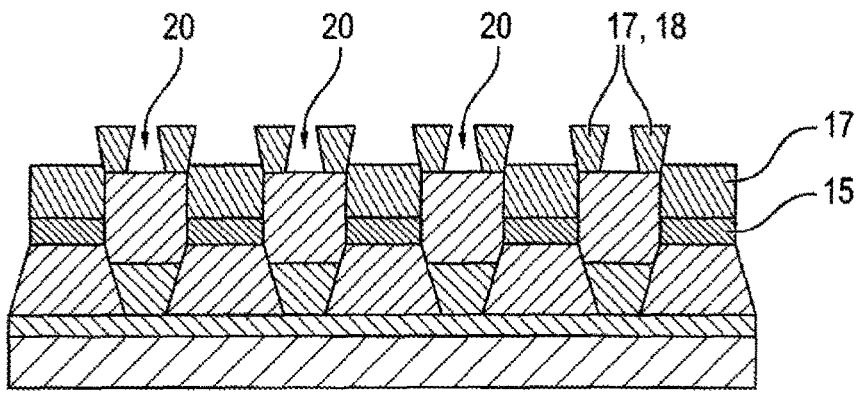
FIG. 12 shows the laminated composite of FIG. 11, wherein the sacrificial material layers has been removed.

FIG. 11 shows the method in a method step after the photoresist layer 16 has been removed. As is shown in FIG. 12, the sacrificial material 15 is subsequently likewise removed, so that voids 20 are created between the masking elements 18. The voids 20 are downwardly delimited by the first material 12 of the medical device to be produced. In the horizontal direction, that is to say the direction which is parallel to the substrate, the voids 20 are delimited by the masking elements 18. The angle of the flanks, which in relation to the first material 12 of the medical device is formed by the masking elements 18, has been molded by the structured photoresist layer 16.

Figure 13:
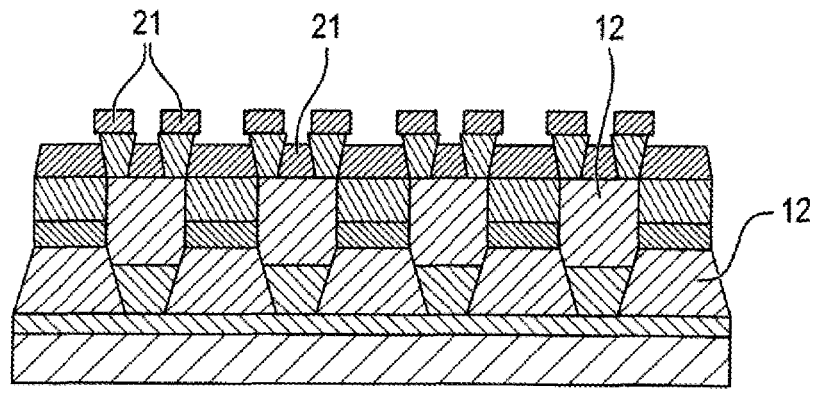
FIG. 13 shows the laminated composite of FIG. 12, wherein a second material of the device to be produced has been deposition-placed.

FIG. 13 shows the method in an intermediate step after a second material 21 has been deposition-placed. The material 21 is uniformly deposition-placed on the entire bare surface and forms a covering layer. In that region in which the first material 12 of the device to be produced prior to deposition-placing of the second material is bare, that is to say in the voids 20, the second material 21 is connected in a materially integral manner to the first material 12 of the device to be produced.

Figure 14:
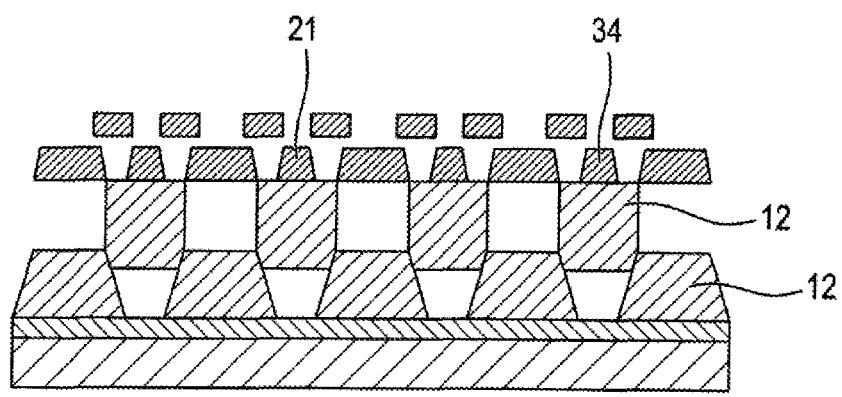
FIG. 14 shows the laminated composite of FIG. 13, wherein the sacrificial material layers have been removed.

In a following step of the method, the sacrificial layers are completely removed. This is performed by means of an etching method. FIG. 14 shows the state after the sacrificial layers 4, 9, 15, 17 have been removed.

Figure 15:
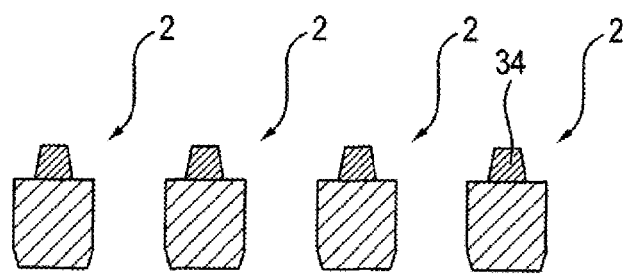
FIG. 15 shows the produced medical device in the section, having surface profiling.

FIG. 15 shows the structural elements 2 in a final state, having a surface profiling 34.

Figure 16:
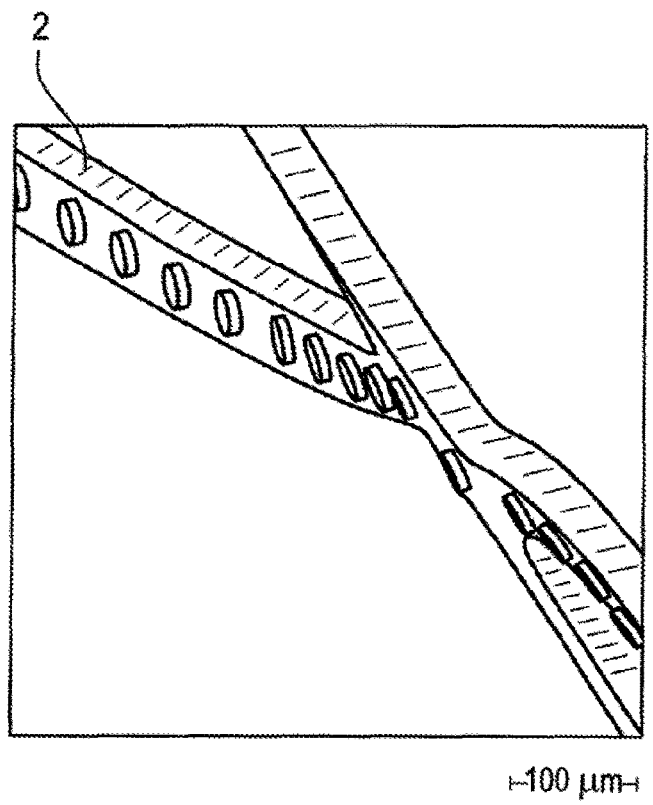
FIG. 16 shows a photograph of the medical device having surface profiling.
Figure 17:
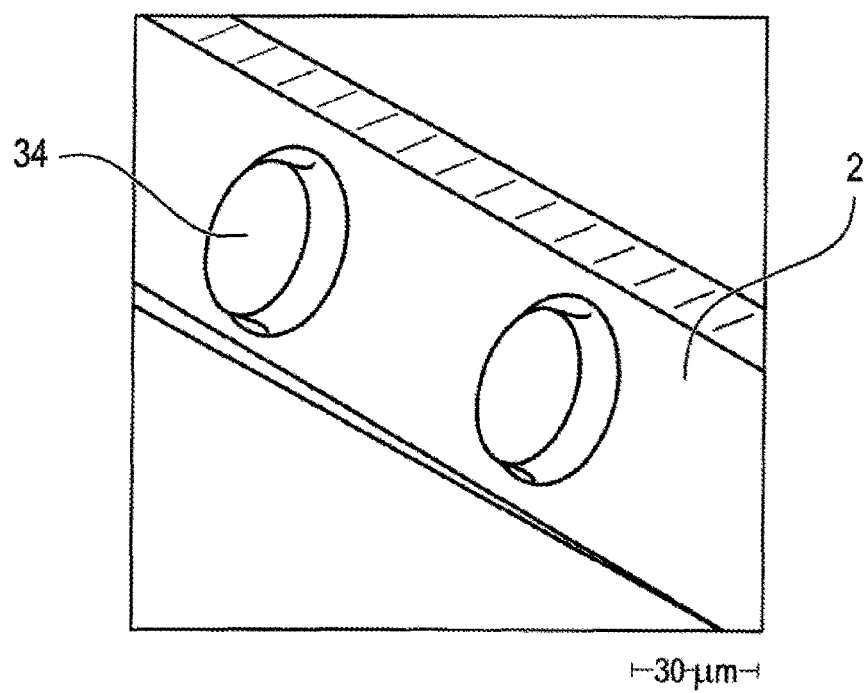
FIG. 17 shows a photograph of the surface profiling of the produced structural elements, in an enlargement.

FIG. 16 shows an example of a medical device, in particular the structural elements 2 of the medical device, having a profiled surface 34 of the structural elements 2. FIG. 17 shows an enlargement of the surface profiling 34. The profiling comprises individual elevations which outwardly project beyond the surface and serve for anchoring the lattice structure in the vessel wall. In the plan view, the elevations are oval. Other geometric shapes are producible. The elevations are disposed behind one another along the structural elements, in particular the webs. The elevations may be formed from the same material as the material of the webs, or from a dissimilar material.

Figure 18:
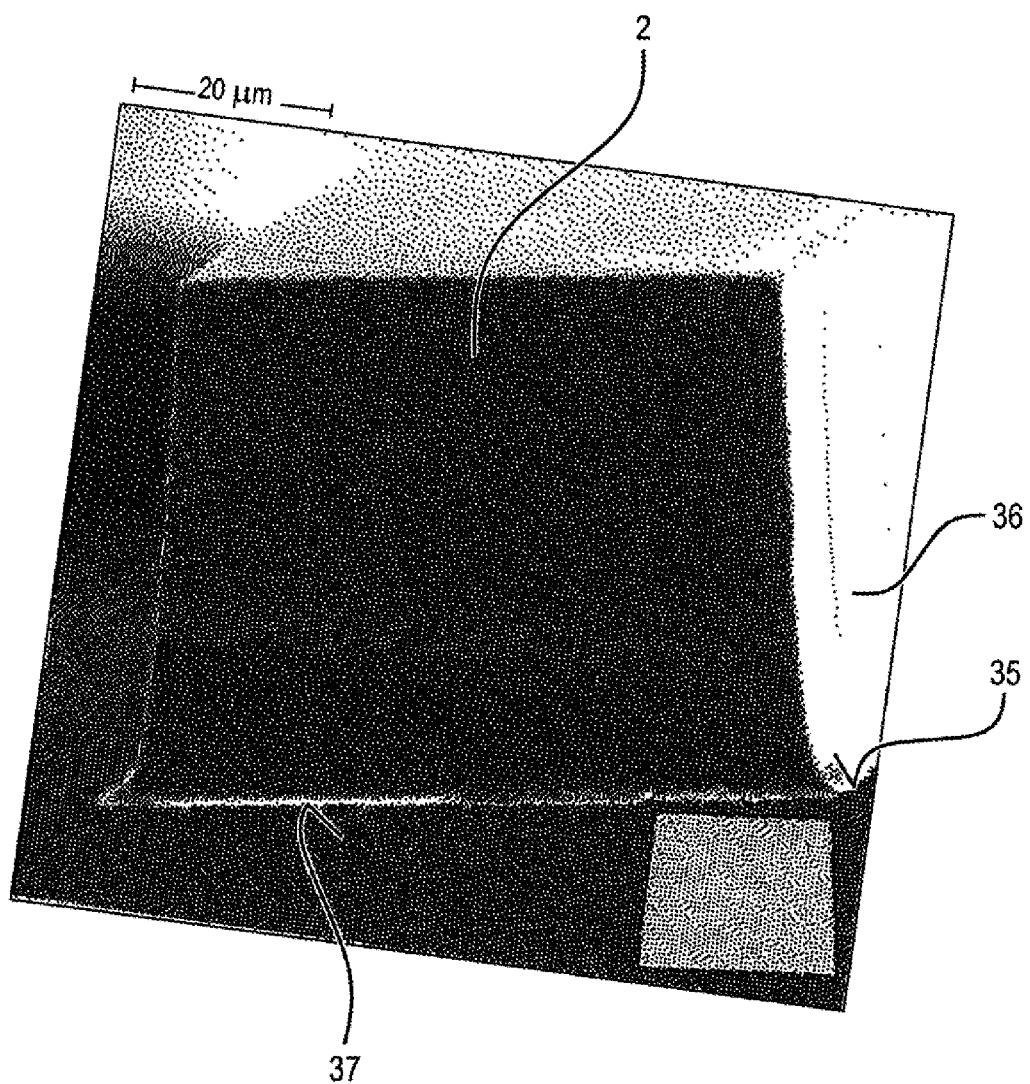
FIG. 18 shows a cross section through a structural element having a trapezoidal cross section, produced according to the invention.

FIG. 18 shows a medical device 1 or the structural elements 2 of the medical device 1, respectively, in the cross section. This structural element illustrated in FIG. 18 has been produced by the method according to the invention. The structural element has slightly inclined lateral walls 36. The lateral walls 36 in the lower region transition into a cutting edge 35. The cutting edge 35 is formed between the base area 37 of the structural element 2 and the inclined lateral wall 36 and has a curved flank which continuously transitions into the straight face of the lateral wall 36. The cutting edge 35 is particularly advantageous for anchoring the medical device in a vessel wall. Since the cutting edge 35 forms the external edge of the structural element 2, the former may be used for releasing and removing debris and blood clots. The structural element 2 produced by the method according to the invention may thus be a web of a cutting element, in particular a sharp-edged web of a retriever, that is to say of a thrombectomy device.

The structural element 2 according to FIG. 18 has been formed using a laminated composite 28, the masking elements of which having a comparatively large mutual spacing 25. Therefore, the structural element 2 of FIG. 18 in terms of the base area 37 thereof is comparatively wide.

Figure 19:
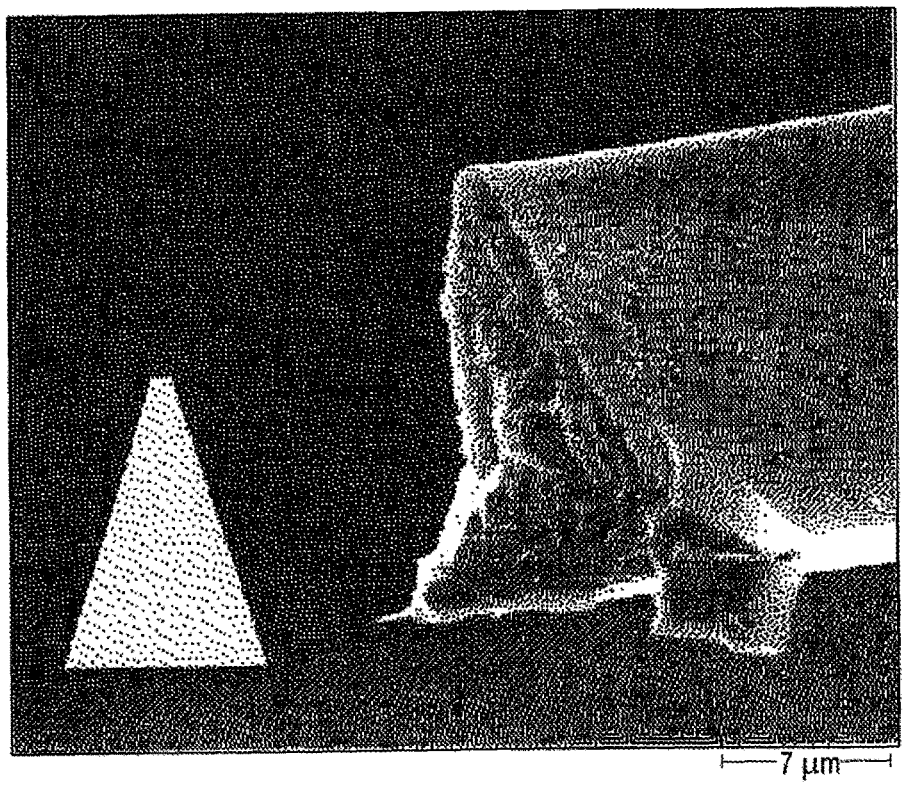
FIG. 19 shows a cross section through a structural element having a triangular cross section, produced according to the invention.
Figure 20:
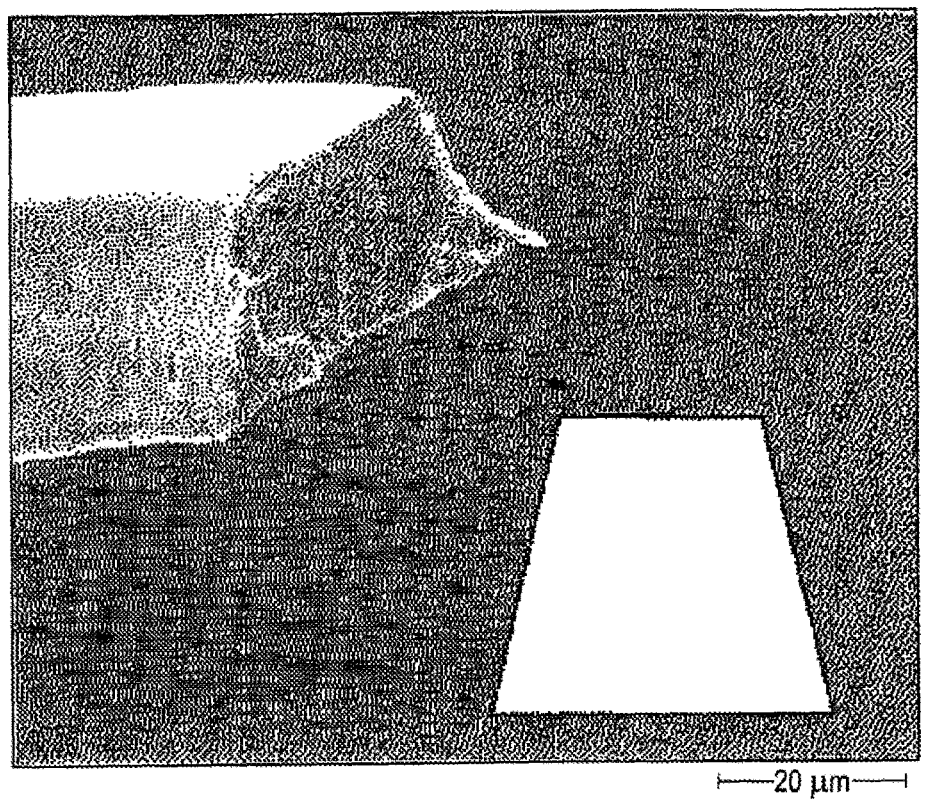
FIG. 20 shows a cross section through a structural element having a trapezoidal cross section and having more highly inclined lateral wall, produced according to the invention.

In comparison, the structural element of FIG. 19 is designed so as to be almost triangular. Said structural element has a comparatively small base area, lateral walls which are somewhat more heavily inclined, and an almost pointed upper side. FIG. 20 shows a structural element 2 which is formed so as to have a trapezoidal cross section.

A further method by way of which surface profiling of a device, for example of a medical device, is possible is shown in individual selected method steps in FIGS. 8 and 21 to 27. FIG. 6 shows the medical device or the structural elements 2, respectively, as still being disposed on the laminated composite of FIG. 4 or FIG. 5, respectively. As is shown in FIG. 8, a further sacrificial material 15 is deposition-placed on the structural elements 2. The sacrificial material 15 covers the entire first material 12 of the device to be produced.

Figure 21:
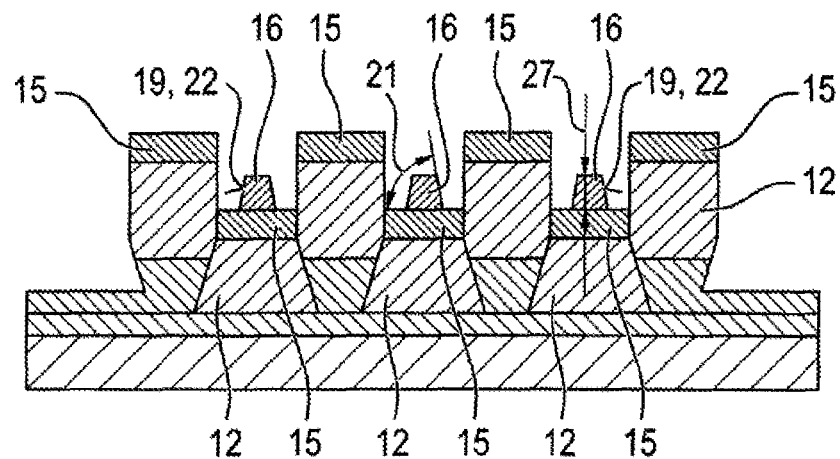
FIG. 21 shows the laminated composite of FIG. 8, wherein a structured photoresist has been applied.

FIG. 21 shows the next method step for producing a surface profile of the structural elements 2 to be produced. An already structured further photoresist layer 16 is shown. The lateral faces 22 of the further photoresist layer 16 in relation to the further sacrificial material layer 15 form an angle 21. The structuring of the photoresist layer 16 or the external contour 19 of the structural further photoresist layer 16 substantially forms a positive image of the desired surface profiling 34 of the structural element to be produced. The structured photoresist layer 16 may form insular elevations, for example, which are disposed so as to be distributed along the surface of the structural elements. In the example illustrated, the structured photoresist layer 16 is embodied in the form of insular elevations on the lower-lying sacrificial material layers 15. This shape corresponds to the profile of the modified surface of the structural elements 2. Suitable structuring of the photoresist layer enables any other surface profiles.

Figure 22:
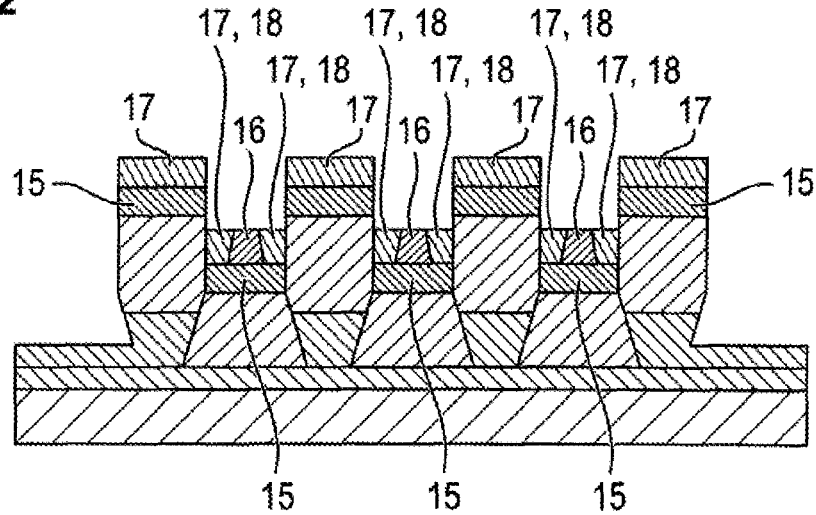
FIG. 22 shows the laminated composite of FIG. 21, wherein a further sacrificial material layer has been applied.

FIG. 22 shows the subsequent method step in which a further sacrificial material layer 17 has been applied. The sacrificial material layer 17 forms further masking elements 18 which are formed around the photoresist layer 16. The internal contour of the masking elements 18 corresponds to the external contour 19 of the structured photoresist layer.

Figure 23:
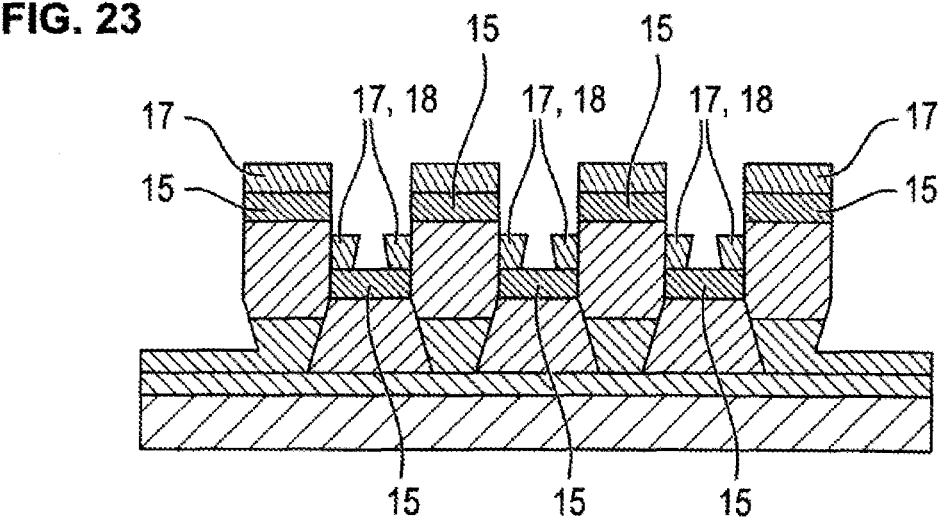
FIG. 23 shows the laminated composite of FIG. 22, wherein the photoresist layer has been removed.
Figure 24:
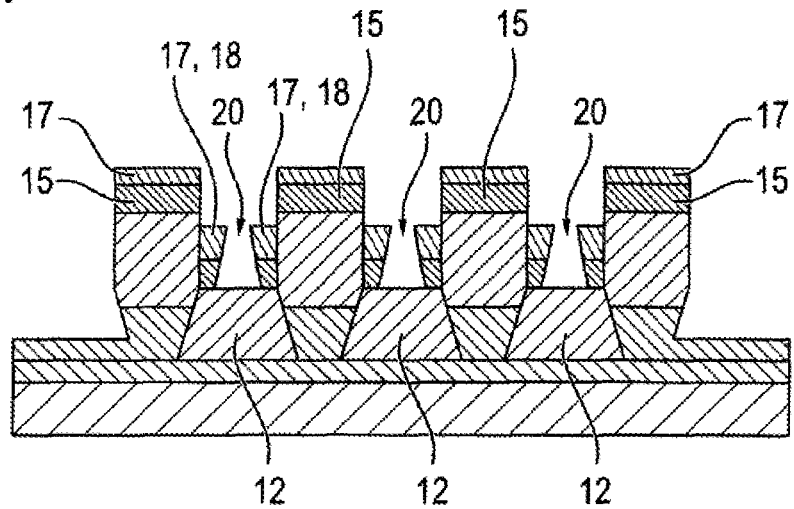
FIG. 24 shows the laminated composite of FIG. 23, wherein the sacrificial material layer has been removed in portions.

FIG. 23 shows the method in a method step after the photoresist layer 16 has been removed. As is shown in FIG. 24, the sacrificial material 15 is subsequently likewise removed in portions, so that voids 20 are created between the masking elements 18. The sacrificial material 15 in the illustrated exemplary embodiment is removed in the lower-lying portions of the sacrificial material layers 15, namely in those portions on which the photoresist layer 16 has previously been applied. The voids 20 are downwardly delimited by the first material 12 of the (medical) device to be produced. In the horizontal direction, that is to say the direction which is parallel to the substrate, the voids 20 are delimited by the masking elements 18. The angle of the flanks, which in relation to the first material 12 of the medical device is formed by the masking elements 18, has been molded by the structured photoresist layer 16.

Figure 25:
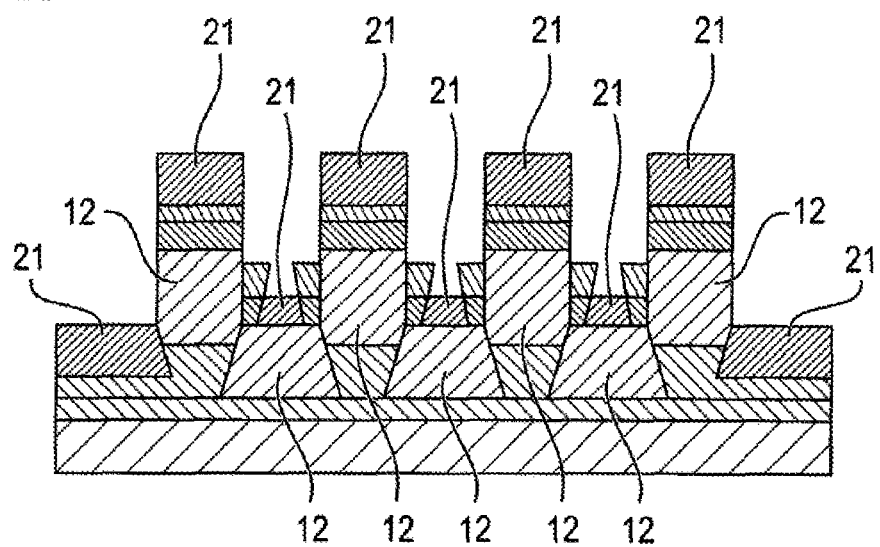
FIG. 25 shows the laminated composite of FIG. 24, wherein a second material of the device to be produced has been deposition-placed.

FIG. 25 shows the method in an intermediate step after a second material 21 has been deposition-placed. The material 21 is uniformly deposition-placed on the bare surface, in particular on the illustrated surface which is disposed so as to be elevated, and forms a covering layer. In that region in which the first material 12 of the device to be produced prior to deposition-placing of the second material is bare, that is to say in the voids 20, the second material 21 is connected in a materially integral manner to the first material 12 of the device to be produced.

Figure 26:
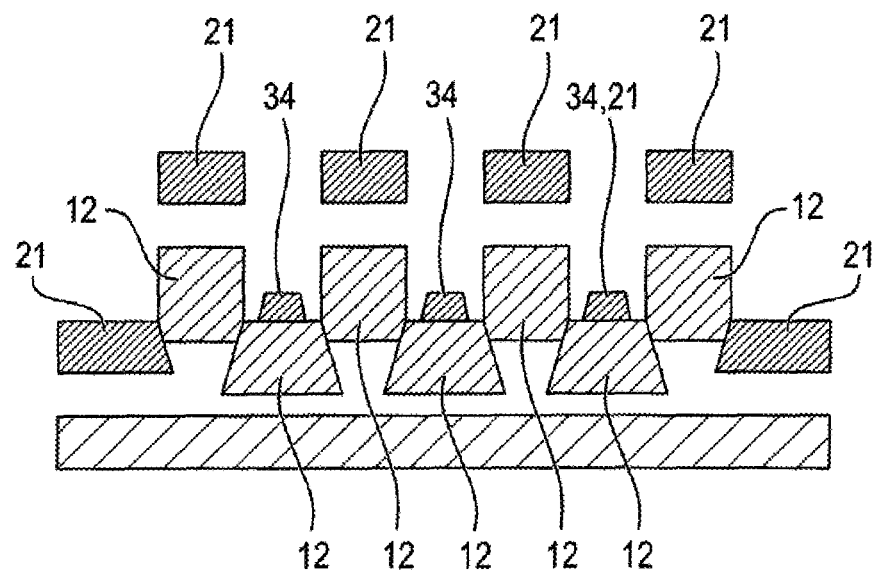
FIG. 26 shows the laminated composite of FIG. 25, wherein the sacrificial material layers have been removed.

In a following step of the method, the sacrificial layers are completely removed. This is performed by means of an etching method. FIG. 26 shows the state after the sacrificial layers 4, 9, 15, 17 have been removed.

Figure 27:
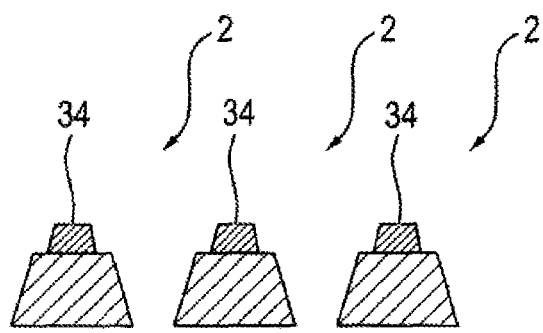
FIG. 27 shows the produced (medical) device in the section, having a surface profile.

FIG. 27 shows the structural elements 2 in a final state, having a surface profiling 34.

LIST OF REFERENCE SIGNS

1 Medical device
2 Structural element
3 Substrate
4 First sacrificial material
5 Photoresist layer
6 First voids
7 Lateral faces of the photoresist layer 5
8 Angle between the lateral faces and the substrate
9 Sacrificial material
10 First masking elements
11 Second voids
12 First material of the device to be produced
13 Internal contour of the first voids 6
14 Flanks of the first masking elements 10
15 Further sacrificial material layer
16 Further photoresist layer
17 Sacrificial material
18 Masking element
19 External contour of the structured further photoresist layer
20 Third void
21 Angular faces between the lateral faces 22 and the further photoresist layer 16
22 Lateral faces of the further photoresist layer 16
23 Height of the masking elements
24 Height of the structural elements 2 to be produced
25 Spacing of the first masking elements 10
26, 27 Height of the photoresist layer 5, 16
28 Laminated composite
29 Angle of the flanks
30 Lateral walls of the device 1 to be produced
31 Angle of the lateral walls 30 of the device 1 to be produced
32 Width of a structural element 2
33 Upper side of the masking elements
34 Surface profiling
35 Cutting edge
36 Lateral walls of a structural element 2
37 Base area of a structural element 2

What is claimed is:

1. A method for producing a device, the device comprising a plurality of structural elements, the method comprising the steps of:
   (a) providing a substrate;
   (b) depositing a first sacrificial material layer on the substrate, the first sacrificial layer comprising a first sacrificial material;
   (c) depositing a first photoresist layer on the first sacrificial material layer to form a plurality of first voids to define a shape of a first structural element of the plurality of structural elements, a first plurality of lateral faces defining each first voids, the first plurality of lateral faces laying in a face plane that intersects a substrate plane at a predetermined angle, the substrate plane defining a top surface of the substrate, each of the plurality of first voids comprising an internal contour of the first photoresist layer;
   (d) depositing a second sacrificial material layer into the plurality of internal contours to form a plurality of first masking elements in the plurality of the first voids, the second sacrificial material layer comprising a second sacrificial material;
   (e) removing the first photoresist layer to expose a plurality of second voids, the plurality of second voids being disposed between the first masking elements of the plurality of first masking elements;
   (f) depositing a first structural material in the second voids and on an upper surface of the first masking elements to form the first structural element; and
   (g) removing the second sacrificial material layer to leave the first structural element.

2. The method as claimed in claim 1, wherein the predetermined angle is in a range between 45° to less than 90°.

3. The method as claimed in claim 1, wherein the respective plurality of lateral faces of at least one first void defines a funnel shape.

4. The method as claimed in claim 1, wherein at least some of the first masking elements comprise sides that are inclined to correspond to the predetermined angle of the lateral faces.

5. The method as claimed in claim 1, wherein the first photo-resist layer comprises a lattice structure.

6. The method as claimed in claim 1, further comprising, after step (f), performing the following steps to obtain a second structural element:

(g) depositing a third sacrificial material layer on the structural material, the third sacrificial layer comprising a third sacrificial material;

(h) depositing a second photoresist layer on the third sacrificial material layer to form a plurality of third void to define a shape of a second structural element of the plurality of structural elements, a second plurality of lateral faces defining each third voids, the second plurality of lateral faces laying in the face plane, each of the plurality of third voids comprising an external contour of the second photoresist layer;

(i) depositing a fourth sacrificial material layer onto the third sacrificial layer to form a plurality of second masking elements on the external counter, the fourth sacrificial material layer comprising a fourth sacrificial material;

(j) removing the second photoresist layer and the third sacrificial material layer to expose a plurality of fourth voids, the plurality of fourth voids being disposed between the second masking elements of the plurality of first masking elements;

(k) depositing a second structural material in the third voids and on a upper surface of the second masking elements; and (l) removing all sacrificial material layers to leave the first and the second structural elements.

7. The method as claimed in claim 6, wherein at least some of the second masking elements comprise sides that are inclined to correspond to the predetermined angle of the lateral faces.

8. The method as claimed in claim 6, wherein each of the sacrificial materials are electrically conducting and each of the masking layers are electrochemically deposited on the respective sacrificial material layer.

9. The method as claimed in claim 6, wherein steps (f) and (l) are performed by sputtering.

10. The method as claimed in claim 6, wherein a maximum height of the first structural element and second structural element correlates to a height of the respective masking element.

11. The method as claimed in claim 6, wherein a maximum width of the first structural element and second structural element correlates to a width of the respective masking element.

12. The method as claimed of claim 6, wherein a height of the first structural element or the second structural element is 2 to 300 µm.

13. The method as claimed of claim 1, wherein the first structural material is selected from the group of a shape-memory material, NiTi, a heavy metal, tantalum, or an electrically conducting material, a magnetic material, a piezoelectric material or an isolating material.

14. The method as claimed in claim 1, wherein the first sacrificial material is identical to the second sacrificial material.

15. The method as claimed in claim 1, wherein step (f) is performed by vapor deposition.

16. The method as claimed in claim 1, wherein the medical device is selected from the group of actuators, micro pumps, linear actuators in the field of microsystems technology, actuators for minimally invasive instruments, micro actuators, and flexible micro antennae.

17. A method of modifying the surface of a medical device,
the medical device comprises a plurality of structural element, the medical device having an outer surface,
the method comprising the steps of:
  (a) providing the medical device;
  (b) depositing a first sacrificial material layer on the outer surface, the first sacrificial layer comprising a first sacrificial material;
  (c) depositing a first photoresist layer on the first sacrificial material layer to form a plurality of first voids to define a shape of a first structural element of the plurality of structural elements, a first plurality of lateral faces defining each first voids, the first plurality of lateral faces laying in a face plane that intersects a substrate plane at a predetermined angle, the substrate plane defining a top surface of the substrate, each of the plurality of first voids comprising an internal contour of the first photoresist layer;
  (d) depositing a second sacrificial material layer into the plurality of internal contours to form a plurality of first masking elements in the plurality of the first voids, the second sacrificial material layer comprising a second sacrificial material;
  (e) removing the first photoresist layer to expose a plurality of second voids, the plurality of second voids being disposed between the first masking elements of the plurality of first masking elements;
  (f) depositing a first structural material in the second voids and on an upper surface of the first masking elements to form the first structural element; and
  (g) removing the second sacrificial material layer to leave the first structural element.

18. The method of claim 17, wherein the medical device is selected from the group of actuators, micro pumps, linear actuators in the field of microsystems technology, actuators for minimally invasive instruments, micro actuators, and flexible micro antennae.

* * * * *